United States Patent
Li et al.

(10) Patent No.: US 11,213,411 B2
(45) Date of Patent: Jan. 4, 2022

(54) SHAPE MEMORY MATERIAL-BASED MINIMALLY INVASIVE IMPLANTATION WITH END PART SELF-EXPANDING STRUCTURE

(71) Applicant: TSINGHUA UNIVERSITY, Beijing (CN)

(72) Inventors: Luming Li, Beijing (CN); Linze Li, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 179 days.

(21) Appl. No.: 16/463,993

(22) PCT Filed: Dec. 18, 2017

(86) PCT No.: PCT/CN2017/116996
§ 371 (c)(1),
(2) Date: May 24, 2019

(87) PCT Pub. No.: WO2018/153148
PCT Pub. Date: Aug. 30, 2018

(65) Prior Publication Data
US 2020/0383808 A1    Dec. 10, 2020

(30) Foreign Application Priority Data

Feb. 24, 2017  (CN) .......................... 201710103659.3

(51) Int. Cl.
*A61F 2/82*    (2013.01)
*A61B 17/00*   (2006.01)
(Continued)

(52) U.S. Cl.
CPC .......... *A61F 2/82* (2013.01); *A61B 17/00234* (2013.01); *A61B 17/80* (2013.01);
(Continued)

(58) Field of Classification Search
CPC combination set(s) only.
See application file for complete search history.

(56) References Cited

U.S. PATENT DOCUMENTS 5,824,054 A * 10/1998 Khosravi ................. A61F 2/92
623/1.44
5,824,082 A * 10/1998 Brown ................. A61F 2/0063
623/11.11
(Continued)

FOREIGN PATENT DOCUMENTS

| CN | 1529571 A | 9/2004 |
|---|---|---|
| CN | 103107732 A | 5/2013 |
| CN | 106955420 A | 7/2017 |

OTHER PUBLICATIONS

International Search Report dated Mar. 22, 2018 in corresponding International Application No. PCT/CN2017/116996; 4 pages.

*Primary Examiner* — Yashita Sharma
(74) *Attorney, Agent, or Firm* — Grossman, Tucker, Perreault & Pfleger, PLLC

(57) ABSTRACT

A shape memory material-based minimally invasive implantation with end part self-expanding structure, and an implant having the structure. The implant includes an actuating component; the implant has a first shape and a second shape, and comprises a central part and multiple end parts which are substantially symmetrically distributed; the second shape has a larger area than the first shape; the actuating component is able to enable the end parts to move along a direction away from the central part of the implant, so that the implant is transformed from the first shape to the second shape. The present invention can allow an implant to have a small size before it is implanted and to be expanded into a structure having a larger size after implantation.

16 Claims, 7 Drawing Sheets

(a)

(b)

(51) Int. Cl.
     *A61N 1/375*      (2006.01)
     *A61B 17/80*      (2006.01)
     *A61B 17/84*      (2006.01)
     *A61F 2/06*      (2013.01)
     *A61F 2/16*      (2006.01)
     *A61F 2/32*      (2006.01)
     *A61F 2/38*      (2006.01)
     *A61F 2/30*      (2006.01)
     *A61M 25/00*      (2006.01)
     *A61N 1/39*      (2006.01)

(52) U.S. Cl.
     CPC ... *A61B 17/846* (2013.01); *A61B 2017/00004* (2013.01); *A61B 2017/00867* (2013.01); *A61F 2/06* (2013.01); *A61F 2/16* (2013.01); *A61F 2/32* (2013.01); *A61F 2/38* (2013.01); *A61F 2002/30092* (2013.01); *A61F 2210/0014* (2013.01); *A61M 25/00* (2013.01); *A61M 2205/0266* (2013.01); *A61N 1/37512* (2017.08); *A61N 1/37514* (2017.08); *A61N 1/39* (2013.01)

(56) References Cited

U.S. PATENT DOCUMENTS

2005/0165480 A1*   7/2005   Jordan ............. A61B 17/12181
                                                                                623/9
2011/0144667 A1*   6/2011   Horton ................... A61L 31/10
                                                                                606/151

* cited by examiner (a)

(b)

(a)

(b)

(c)

(d)

(a)                  (b)

(c)                  (d)

(a)

(b)

(c)

(d)

(a)          (b)

(a)          (b)          (c)

218# SHAPE MEMORY MATERIAL-BASED MINIMALLY INVASIVE IMPLANTATION WITH END PART SELF-EXPANDING STRUCTURE

This application claims all benefits from China Patent Application No. 201710103659.3, titled "SHAPE MEMORY MATERIAL-BASED MINIMALLY INVASIVE IMPLANTATION WITH END PART SELF-EXPANDING STRUCTURE", filed on Feb. 24, 2017, in the China Intellectual Property Office, the disclosure of which is incorporated herein by reference

FIELD

This invention relates to a shape memory material-based minimally invasive implantation with end part self-expanding structure, belong to implantable medical device (IMD) technology field.

BACKGROUND

Implantable medical device generally refers to a medical device that is partly or entirely implanted into the human body or natural canal by means of surgery. After the operation, the implantable medical device will stay in the body for a long time, usually for at least 30 days. Implanted medical device belongs to the high-end products of the third category of medical devices and is an important product in the medical device industry. Currently, the implanted medical devices, that are widely applied, can be active and passive implantable medical devices, such as heart pacemakers, defibrillators, deep brain stimulation (DBS), stents, catheters, artificial valves, artificial cochlea, artificial blood vessels, intraocular lenses, artificial hip joints, artificial knee joints, bone plates, bone nails and other implants.

In the process of medical device implantation, it is inevitable to cut an incision, so that the medical device can be implanted into the body. On the one hand, the relatively larger incision may cause greater surgical risk to patients during the operation. On the other hand, the relatively larger incision also may cause greater chance of infection and pain after the operation. Therefore, what is needed is a structure that can be implanted into the body through a relatively smaller incision, expand to have a larger surface, and deployed to a larger area after implantation, so that to achieve the required function.

SUMMARY

A shape memory material-based minimally invasive implantation with end part self-expanding structure, comprises a shape memory self-expanding structure and a functional module. The shape memory self-expanding structure consists of shape memory material and is in first shape before being implanted in body. The first shape substantially expands along a single axis or a plurality of axes, and forms two end parts at opposite sides of the axis. The second shape has a larger area than that of the first shape. The two end parts move along a direction substantially perpendicular to the axis, so that the implant can be transformed from the first shape to the second shape. Based on the elasticity and/or memory effect of the shape memory material, the self-expanding structure is a small size structure before being implanted and would be caused to expand to be a large size structure and deployed on a larger area after being implanted by the releasing constraint, changing temperature, light illumination, electromagnetic irradiation, or chemical induce. The functional module can include circuit, battery, sensor, energy collector or other device.

An implant is provided in this invention. The implant comprises an actuating member, wherein the implant has a first shape and a second shape; the implant has a central portion and a plurality of end parts substantially symmetrically arranged; the second shape having a larger area than that of the first shape, and the actuating member is capable of causing the plurality of end parts to move along a direction away from the central portion, so that the implant is transformed from the first shape to the second shape.

Furthermore, the actuating member comprises a stretchable structure between the end points of the plurality of end parts.

Furthermore, the actuating member comprises a stretchable structure between each of the plurality of end parts and the central portion of the implant.

Furthermore, the actuating member comprises a stretchable structure between the plurality of end parts.

Furthermore, the stretchable structure comprises a foldaway stretchable structure or a wavy stretchable structure.

Furthermore, the stretchable structure comprises a plurality of sheet-shaped portions.

Furthermore, the first shape formed by the plurality of sheet-shaped portions is cylindrical, and the second shape is substantially the rectangular.

Furthermore, the stretchable structure comprises a shape memory material.

Furthermore, the implant further comprises a functional module.

Furthermore, the functional module comprises a wireless energy transfer unit.

Furthermore, the wireless energy transfer unit comprises a foldable flexible portion.

Furthermore, the implant further comprises a constraint unit configured to keep the implant in the first shape.

Furthermore, the constraint unit is made of biodegradable material.

Furthermore, the wireless energy transfer unit is selected from the group consisting of photovoltaic cell array, piezoelectric electric generator, friction electric generator, thermoelectric electric generator, electromagnetic electric generator, and vibration electric generator.

Furthermore, the wireless energy transfer unit has a single layer or a plurality of layers, and a separating membrane is located or not located between adjacent two layers.

Furthermore, outer surface of the wireless energy transfer unit is coated by at least one biocompatible film.

Furthermore, at least one of the actuating member and the wireless energy transfer unit defines one or more than one through hole.

Furthermore, comprising a plurality of units, the plurality of units are connected with each other by conductive wires, and each unit comprises the actuating member and the functional module.

An implantable medical device is also provided. The implantable medical device comprises: the implant provided above and an implantable main portion, and the implant and the implantable main portion are connected with each other by conductive wire.

DETAILED DESCRIPTION

References will now be made to the drawings to describe, in detail, various embodiments of the shape memory material-based minimally invasive implantation with end part self-expanding structures provided by this invention.

The shape memory material has the properties of elasticity and memory effect. By changing the constraints, temperature, light illumination, electromagnetic irradiation, chemical induction, and other external conditions, it can make the shape memory material realize structural automatic self-transformation. The specific using method includes but not limited to:

1) Elastic self-expanding type

Based on the elasticity of the shape memory material, the shape memory material is first constrained by compressing, and then the constraint is released after being implanted in body, so that the shape memory material realizes self-expanding.

2) Memory effect self-expanding type

Based on the memory effect of the shape memory material, the shape memory material is first soaked in disinfecting ice water, and then the shape memory material is heated by body temperature to expand after being implanted in body.

3) Memory effect and heating expanding type

Based on the memory effect of the shape memory material, after being implanted in body, the shape memory material is heated (illuminated by light, irradiated by electromagnetic wave, or chemical induced to expand. The heating method can be radio frequency, injecting hot physiological saline solution after being implanted, or electrical heating etc.

4) Memory effect and heating shrinking removing type

After being implanted in body, the shape memory material expand due to balloon. Before removing out of the body, the shape memory material is heated (illuminated by light, irradiated by electromagnetic wave, or chemical induced) to shrink.

The shape memory material-based multi-axis curl minimally invasive implantation with end part self-expanding structures provided in this invention can be designed to be different self-expanding structures based on the elasticity and memory effect of the shape memory material. The functional module, such as circuit, battery, sensor, energy collector etc., can be deployed on the self-expanding structure so that the self-expanding structure can have more functions.

The shape memory material-based minimally invasive implantation with end part self-expanding structures provided in this invention are described in following embodiments.

Embodiment 1

Figure 1:
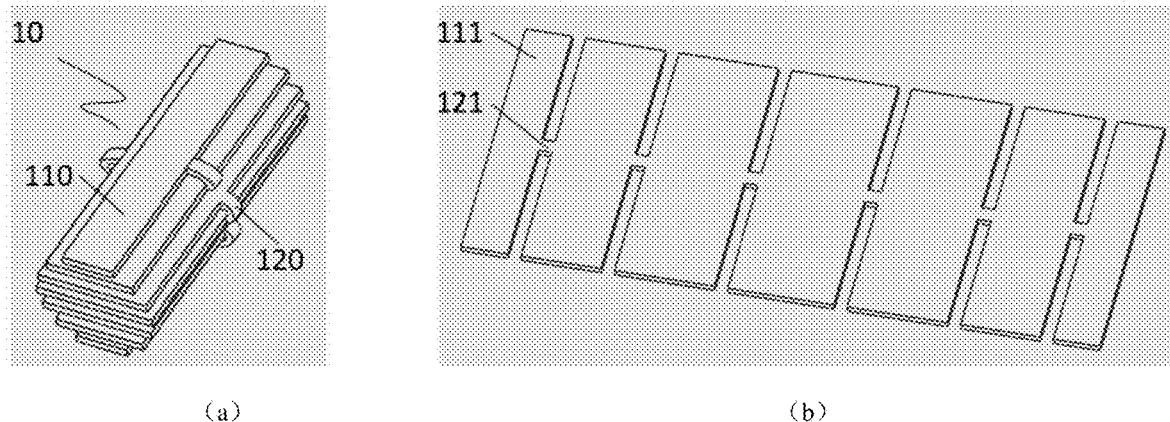
FIG. 1 is a structural schematic view of embodiment 1 of this invention.

Referring to FIG. 1, the shape memory material-based minimally invasive implantation with end part self-expanding structure 10 includes a plurality of sheet-shaped shape memory material-based frames 110 and a plurality of connection portions 120 therebetween. FIG. 1(a) shows the shape of the self-expanding structure 10 before expanding, and FIG. 1(b) shows the shape of the self-expanding structure 10 after expanding. In FIG. 1(a), the plurality of sheet-shaped shape memory material-based frames 110 are stacked with and parallel to each other, and adjacent two of the plurality of sheet-shaped shape memory material-based frames 110 are connected by one of the plurality of connection portions 120. The plurality of sheet-shaped shape memory material-based frames 110 can have the same size and shape, or have different size and shape, so that the stacked sheet-shaped shape memory material-based frames 110 form different shape. As shown in FIG. 1, the entirety of the self-expanding structure 10 is cylindrical, so that it is easy to for implanting the self-expanding structure 10 from the minimally invasive incision of the operation, injecting or implanting vessel. FIG. 1(b) shows the whole shape of the self-expanding structure 10 after expanding, the plurality of sheet-shaped shape memory material-based frames 110 are expanded in parallel toward two directions and deployed in a larger area. Different functional modules, such as a circuit, a battery, a sensor, an energy collector etc., can be deployed on the self-expanding structure 10, so that the self-expanding structure 10 may achieve different functions.

Embodiment 2

Figure 2:
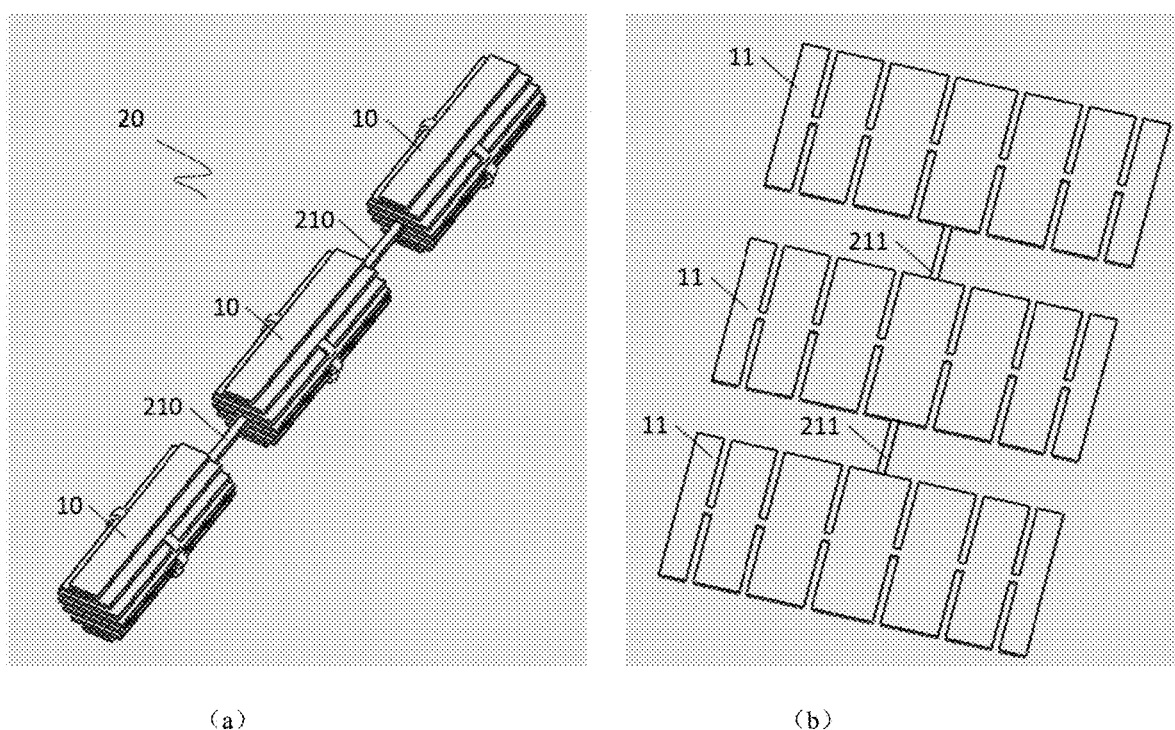
FIG. 2 is a structural schematic view of embodiment 2 of this invention.

Referring to FIG. 2, the shape memory material-based minimally invasive implantation with end part self-expanding structure 20 includes a plurality of end part self-expanding structures 10 of embodiment 1 and a plurality of connection portions 220. FIG. 2(a) shows the shape of the self-expanding structure 20 before expanding, and FIG. 2(b) shows the shape of the self-expanding structure 20 after expanding. In FIG. 2(a), the plurality of end part self-expanding structures 10 are connected by the plurality of connection portions 220 in series to form a slender entire structure. FIG. 1(b) shows the shape of the self-expanding structure 20 after expanding, including the expanded end part self-expanding structures 11 and expanded connection portions 221. The expanded end part self-expanding structures 11 are deployed in a larger area. Different functional modules, such as a circuit, a battery, a sensor, an energy collector etc., can be deployed on the self-expanding structure 20, so that the self-expanding structure 20 may achieve different functions.

Embodiment 3

Figure 3:
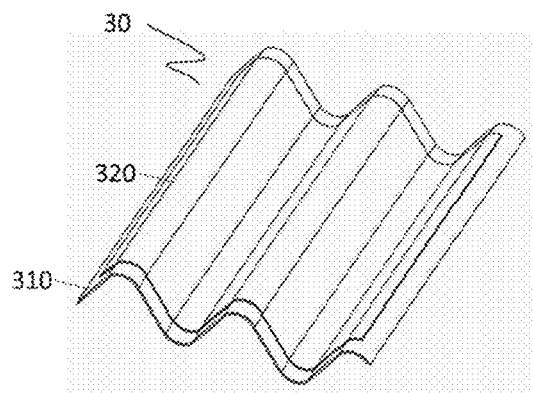
FIG. 3 is a structural schematic view of embodiment 3 of this invention.
Figure 3:
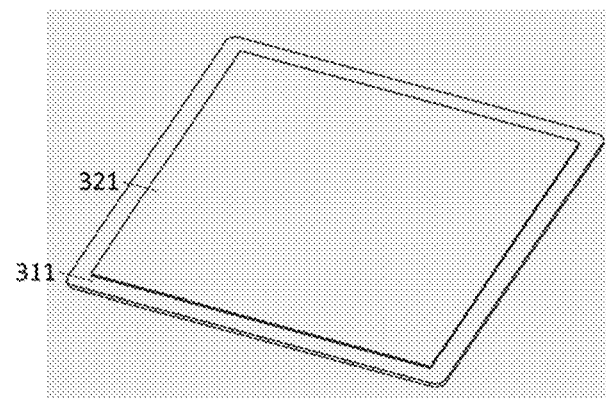

Referring to FIG. 3, the shape memory material-based minimally invasive implantation with end part self-expanding structure 30 includes a wavy shape memory material-based frame 310 and a functional module 320. The functional module 320 is coated on the shape memory material-based frame 310, and the shape memory material-based frame 310 is folded to be wavy before being implanted. FIG. 3(a) shows the shape of the self-expanding structure 30 before being implanted, which e has a small size entirety, and it is easy for minimally invasive implantation. FIG. 3(b) shows the shape of the self-expanding structure 30 after being implanted, the number 311 represents the expanded shape memory material-based frame which forms a larger plane (with different shape) after expanding, the number 321 represents the expanded functional module which forms a larger plane (with different shape) after expanding and is deployed in a larger area.

Embodiment 4

Figure 4:
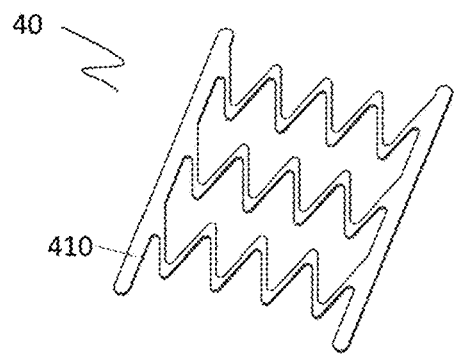
FIG. 4 is a structural schematic view of embodiment 4 of this invention.
Figure 4:
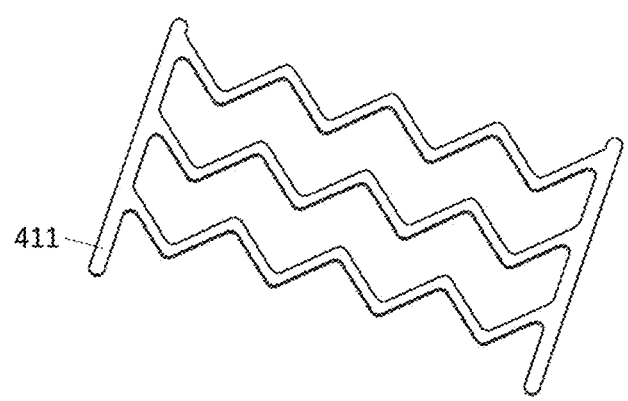
Figure 4:
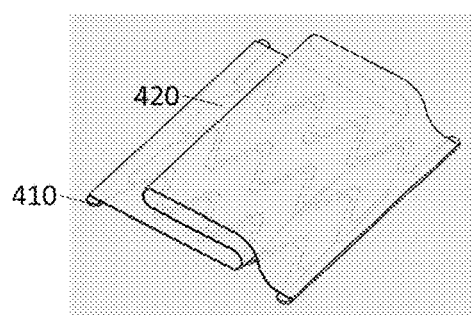
Figure 4:
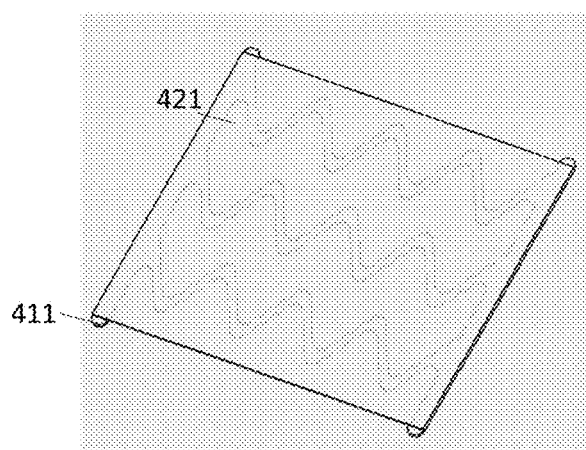

Referring to FIG. 4, the shape memory material-based minimally invasive implantation with end part self-expanding structure 40 includes a shape memory material-based frame 410 and a functional module 420. The functional module 420 is coated on the shape memory material-based frame 410, the shape memory material-based frame 410 consists of a plurality of supports, and the plurality of supports can be in different geometry. FIG. 4(a) shows the shape of the shape memory material-based frame 410 before being implanted in body, and the FIG. 4(c) shows the shape of the whole functional module 420 before being implanted in body, which has a small size entirety, and it is easy for minimally invasive implantation. FIGS. 4(b) and 4(d) show the shape of the self-expanding structure 40 after being implanted, the number 411 represents the expanded shape memory material-based frame, and the expanded shape memory material-based frame 411 expands along opposite directions compare with the shape before being implanted. The number 421 represents the expanded functional module. After being implanted in body, the functional module expands to have a larger surface area and is deployed in a larger area.

Embodiment 5

Figure 5:
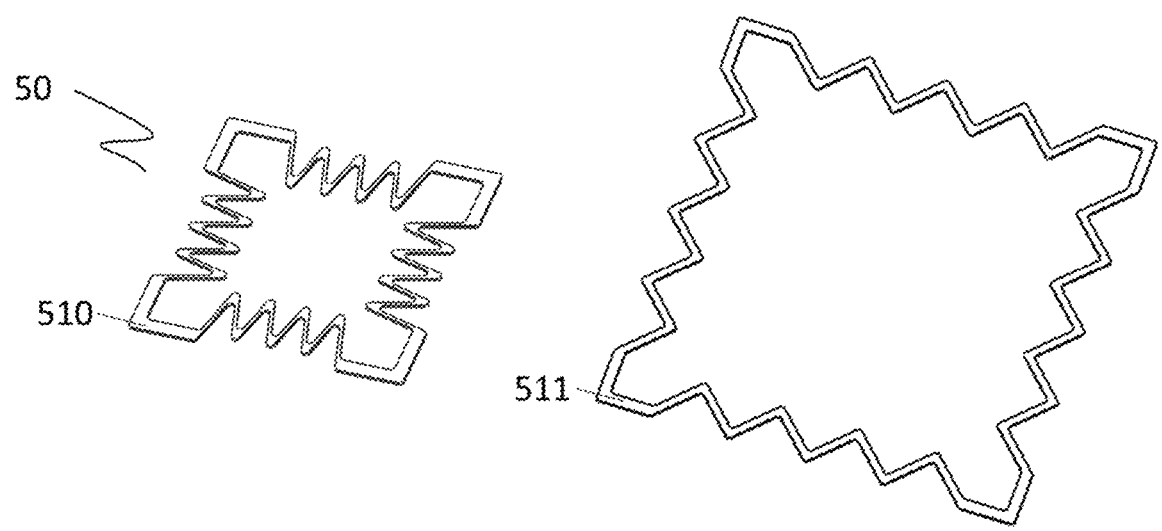
FIG. 5 is a structural schematic view of embodiment 5 of this invention.
Figure 5:
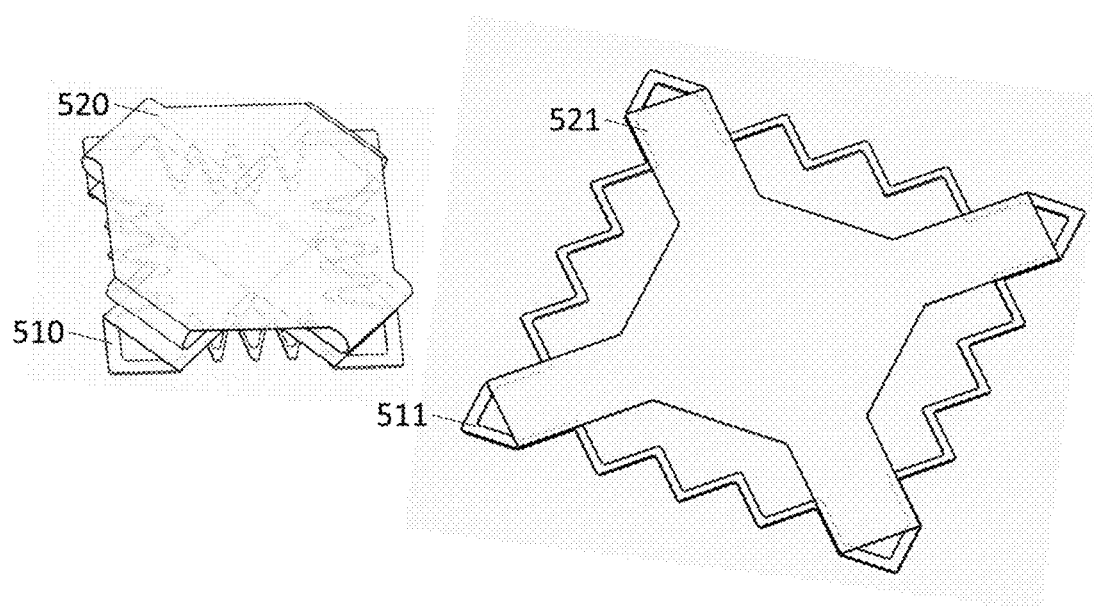

Referring to FIG. 5, the shape memory material-based minimally invasive implantation with end part self-expanding structure 50 includes a shape memory material-based frame 510 and a functional module 520. The functional module 520 is coated on the shape memory material-based frame 510, the shape memory material-based frame 510 consists of a plurality of supports, and the plurality of supports can be in different geometry. FIG. 5(a) shows the shape of the shape memory material-based frame 510 before being implanted in body, and the FIG. 5(c) shows the shape of the whole functional module 520 before being implanted in body, which has a small size entirety, and it is easy for minimally invasive implantation. FIGS. 5(b) and 5(d) show the shape of the self-expanding structure 50 after being implanted, the number 511 represents the expanded shape memory material-based frame, and the expanded shape memory material-based frame 511 expands along opposite directions compare with the shape before being implanted. The number 521 represents the expanded functional module. After being implanted in body, the functional module expands to have a larger surface area and is deployed in a larger area.

Embodiment 6

Figure 6:
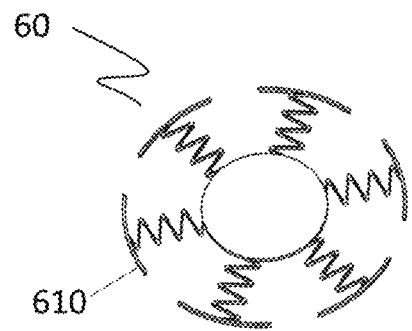
FIG. 6 is a structural schematic view of embodiment 6 of this invention.
Figure 6:
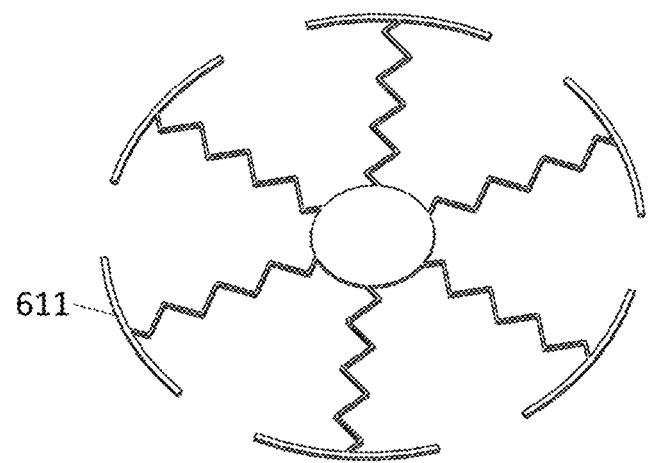
Figure 6:
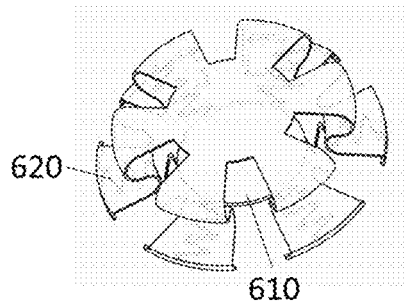
Figure 6:
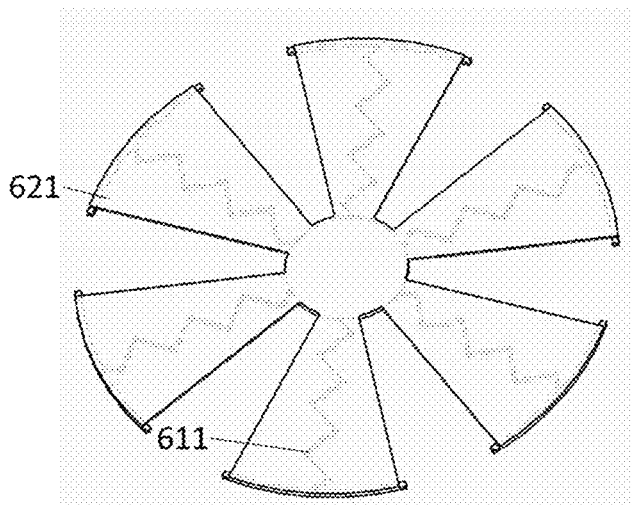

Referring to FIG. 6, the shape memory material-based minimally invasive implantation with end part self-expanding structure 60 includes a shape memory material-based frame 610 and a functional module 620. The functional module 620 is coated on the shape memory material-based frame 610, the shape memory material-based frame 610 consists of a plurality of supports, and the plurality of supports can be in different geometry. FIG. 6(a) shows the shape of the shape memory material-based frame 610 before being implanted in body, and the FIG. 6(c) shows the shape of the whole functional module 620 before being implanted in body, which has a small size entirety, and it is easy for minimally invasive implantation. FIGS. 6(b) and 6(d) show the shape of the self-expanding structure 60 after being implanted, the number 611 represents the expanded shape memory material-based frame, and the expanded shape memory material-based frame 611 expands along six directions (can be n directions, "n" is a natural number) compare with the shape before being implanted. The number 621 represents the expanded functional module. After being implanted in body, the functional module expands to have a larger surface area and is deployed in a larger area.

Embodiment 7

Figure 7:
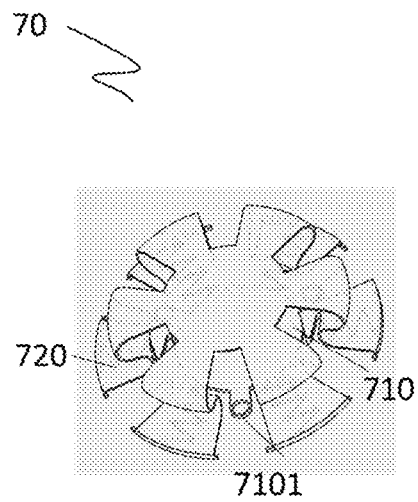
FIG. 7 is a structural schematic view of embodiment 7 of this invention.
Figure 7:
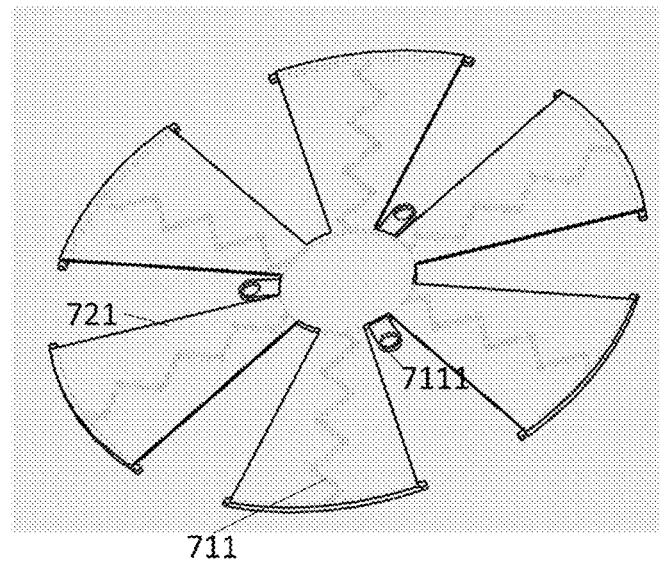

Referring to FIG. 7, the shape memory material-based minimally invasive implantation with end part self-expanding structure 70 includes a shape memory material-based frame 710 and a functional module 720. The functional module 720 is coated on the shape memory material-based frame 710, the shape memory material-based frame 710 consists of a plurality of supports, and the plurality of supports can be in different geometry. The shape memory material-based frame 710 defines a plurality of through holes 7101, and the plurality of through holes 7101 are configured to fix the shape memory material-based frame on the subcutaneous tissue by suturing using suture after being implanted, so that the whole shape memory material-based frame is prevent from dislocation. FIG. 7(a) shows the shape of the whole functional module before being implanted in body, which has a small size entirety, and it is easy for minimally invasive implantation. FIG. 7(b) shows the shape of the self-expanding structure 70 after being implanted, the number 711 represents the expanded shape memory material-based frame, and the expanded shape memory material-based frame 711 expands along six directions (can be n directions, "n" is a natural number) compare with the shape before being implanted. The number 721 represents the expanded functional module. After being implanted in body, the functional module expands to have a larger surface area and is deployed in a larger area.

Embodiment 8

Figure 8:
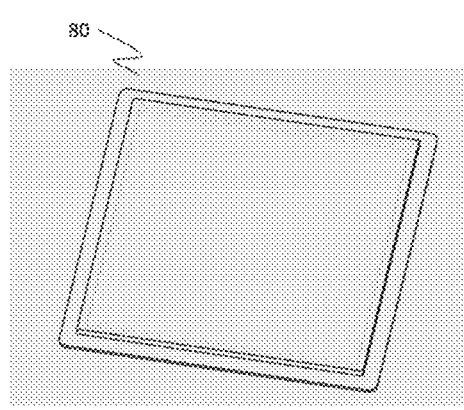
FIG. 8 is a structural schematic view of embodiment 8 of this invention.
Figure 8:
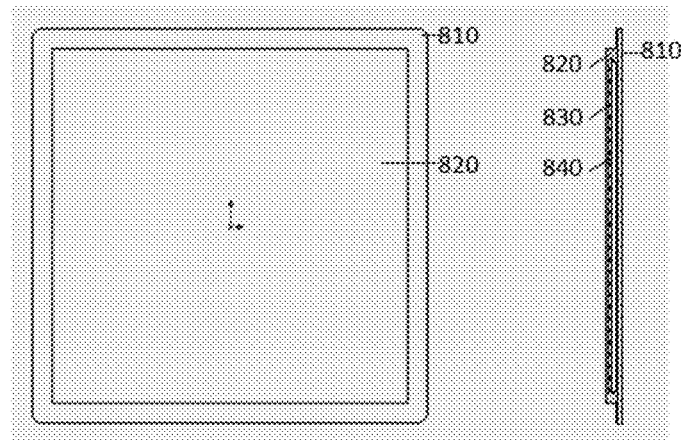

Referring to FIG. 8, the shape memory material-based minimally invasive implantation with end part self-expanding structure 80 includes a shape memory material-based frame 810, a biocompatible flexible material 820, a flexible sealing film 830, and a functional module 840. FIGS. 8(a), 3(b), 3(c) are respectively the 3-dimensional (3D) view of the expanded self-expanding structure 80, top view of the expanded self-expanding structure 80, and cross-sectional view of the expanded self-expanding structure 80. The functional module 840 is deployed on the shape memory material-based frame 810, the outer surface of the functional module 840 is coated by the flexible sealing film 830 and the biocompatible flexible material 820. The flexible sealing film 830 and the biocompatible flexible material 820 respectively play the functions of sealing and improving biocompatibility.

Embodiment 9

Figure 9:
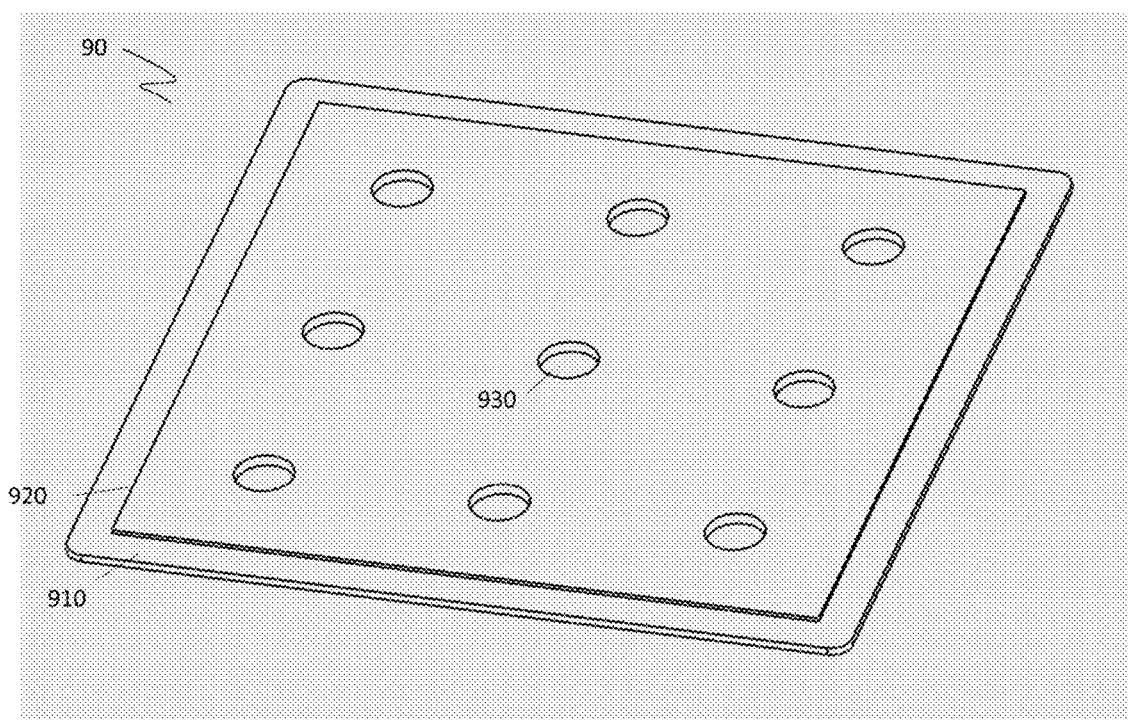
FIG. 9 is a structural schematic view of embodiment 9 of this invention.

Referring to FIG. 9, the shape memory material-based minimally invasive implantation with end part self-expanding structure 90 includes a shape memory material-based frame 910, a functional module 920, and through holes 930. The functional module 920 is coated on the shape memory material-based frame 910. The functional module 920 has a larger surface area and may prevent the growth of the biological tissue. By forming some through holes 930 on the functional module 920, it is beneficial to the growth of biological tissues and the circulation of blood.

Embodiment 10

Figure 10:
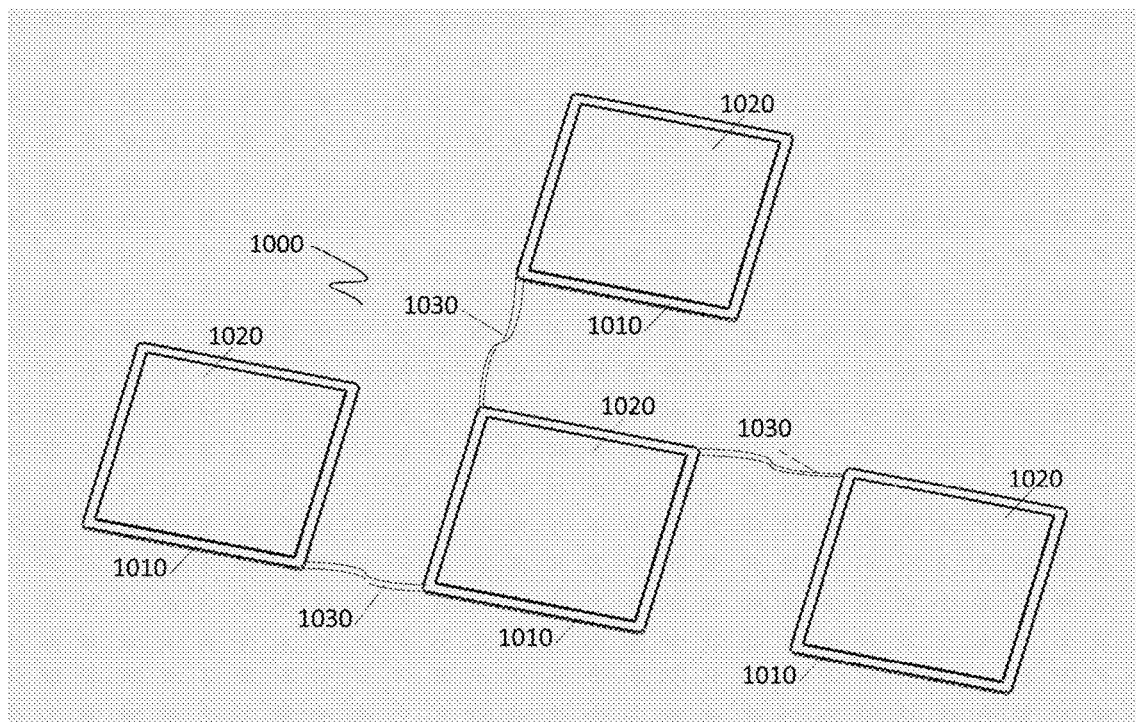
FIG. 10 is a structural schematic view of embodiment 10 of this invention.

Referring to FIG. 10, the shape memory material-based minimally invasive implantation with end part self-expanding structure 1000 includes a plurality of shape memory material-based frames 1010, and a plurality of functional modules 1020. The plurality of functional modules 1020 are deployed on the plurality of shape memory material-based frames 1010. The plurality of shape memory material-based frames 1010 and the plurality of functional modules 1020 are distributed at different positions and can be connected by conductive wires 1030.

Embodiment 11

Figure 11:
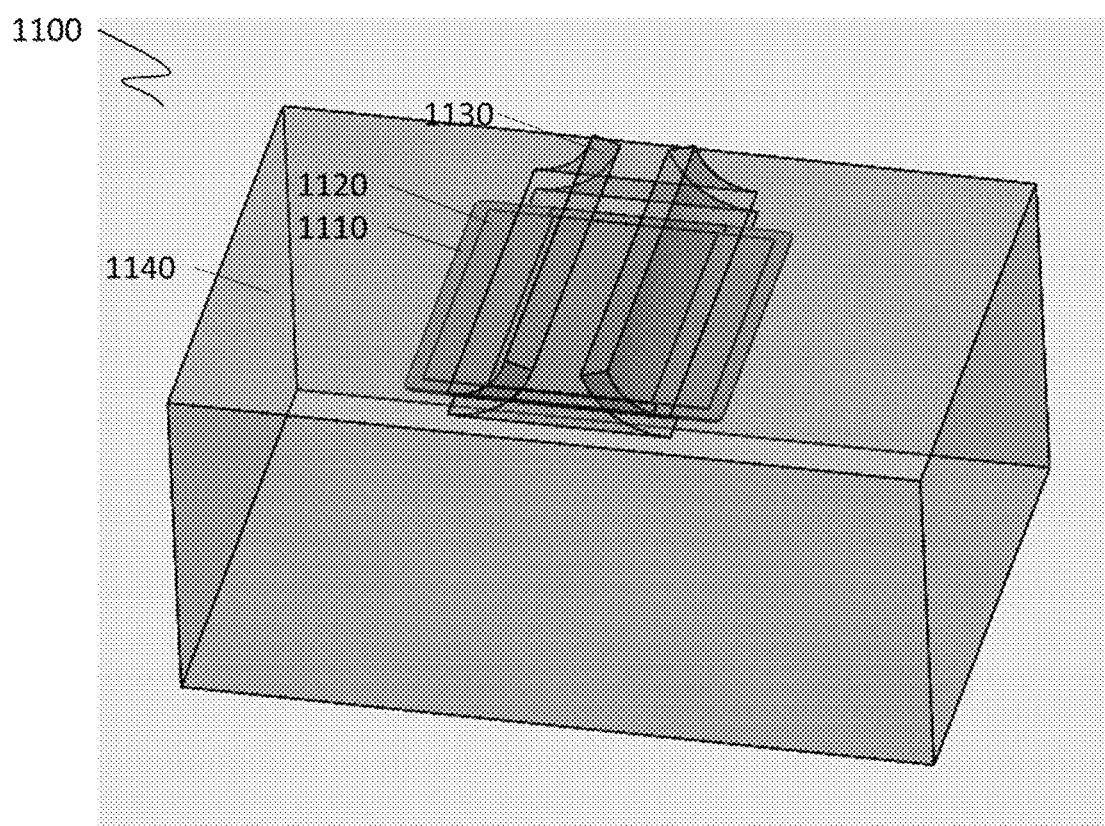
FIG. 11 is a structural schematic view of embodiment 11 of this invention.

Referring to FIG. 11, the shape memory material-based minimally invasive implantation with end part self-expanding structure 1100 includes a shape memory material-based frame 1110 and a functional module 1120. The functional module 1120 is deployed on the shape memory material-based frame 1110. The shape memory material-based minimally invasive implantation with end part self-expanding structure 1100 can be implanted at different subcutaneous positions. The number 1140 represents the skin in different positions (such as hands, neck, head etc.), the number 1130 represents the incision of the skin. Furthermore, when the functional module 1120 is a photovoltaic cell array, in order for receiving more light, the prefer position for the incision of the skin is the position where the light would not be sheltered by the wearing apparel (such as clothes, shoes, hat, etc.).

The invention claimed is:

1. An implant, comprising:
an actuating member, wherein the implant has a first shape and a second shape; the implant has a central portion and a plurality of end parts substantially symmetrically arranged; the second shape having a larger area than that of the first shape, and the actuating member is capable of causing the plurality of end parts to move along a direction away from the central portion, so that the implant is transformed from the first shape to the second shape;
wherein the actuating member comprises at least one foldaway stretchable structure;
wherein the foldaway stretchable structure comprises a plurality of sheet-shaped portions;
wherein the first shape formed by the plurality of sheet-shaped portions is cylindrical, the second shape formed by the plurality of sheet-shaped portions is substantially rectangular; and
wherein the second shape is a flat plane shape and wherein the implant is configured to transition from the first shape to the second shape after being implanted into a human body.

2. The implant as claimed in claim 1, wherein the foldaway stretchable structure is between end parts of the plurality of end parts.

3. The implant as claimed in claim 1, wherein the foldaway stretchable structure is between each of the plurality of end parts and the central portion of the implant.

4. The implant as claimed in claim 1, wherein the foldaway stretchable structure is between the plurality of end parts.

5. The implant as claimed in claim 2, wherein the foldaway stretchable structure comprises a shape memory material.

6. The implant as claimed in claim 1, wherein the implant further comprises a functional module.

7. The implant as claimed in claim 6, wherein the functional module comprises a wireless energy transfer unit.

8. The implant as claimed in claim 7, wherein the wireless energy transfer unit comprises a foldable flexible portion.

9. The implant as claimed in claim 2, wherein the implant further comprises a constraint unit configured to keep the implant in the first shape.

10. The implant as claimed in claim 9, wherein the constraint unit is made of biodegradable material.

11. The implant as claimed in claim 7, wherein the wireless energy transfer unit is selected from the group consisting of photovoltaic cell array, piezoelectric electric generator, friction electric generator, thermoelectric electric generator, electromagnetic electric generator, and vibration electric generator.

12. The implant as claimed in claim 7, wherein the wireless energy transfer unit has a single layer or a plurality of layers, and a separating membrane is located or not located between adjacent two layers.

13. The implant as claimed in claim 7, wherein outer surface of the wireless energy transfer unit is coated by at least one biocompatible film.

14. The implant as claimed in claim 7, wherein at least one of the actuating member and the wireless energy transfer unit defines one or more than one through hole.

15. The implant as claimed in claim 1, further comprising a plurality of units, the plurality of units are connected with each other by conductive wires, and each unit comprises the actuating member and a functional module.

16. An implantable medical device, comprising: the implant as claimed in claim 1 and an implantable main portion, wherein the implant and the implantable main portion are connected with each other by conductive wire.

* * * * *